(12) United States Patent
Nakajima

(10) Patent No.: US 8,672,217 B2
(45) Date of Patent: Mar. 18, 2014

(54) DATA OUTPUT METHOD IN ANALYSIS OF SAMPLE, ANALYTICAL DEVICE, AND ANALYTICAL SYSTEM

(75) Inventor: Shinya Nakajima, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 433 days.

(21) Appl. No.: 12/929,676

(22) Filed: Feb. 8, 2011

(65) Prior Publication Data
US 2011/0204139 A1 Aug. 25, 2011

(30) Foreign Application Priority Data
Feb. 22, 2010 (JP) .................................. 2010-035675

(51) Int. Cl.
*G06F 17/00* (2006.01)

(52) U.S. Cl.
USPC ........................................................ 235/375

(58) Field of Classification Search
USPC ........................................................ 235/375
See application file for complete search history.

(56) References Cited

U.S. PATENT DOCUMENTS

| | | | |
|---|---|---|---|
| 4,678,755 A | 7/1987 | Shinohara et al. | |
| 4,835,372 A | 5/1989 | Gombrich et al. | |
| 4,969,993 A | 11/1990 | Nash, Jr. et al. | |
| 5,424,212 A | 6/1995 | Pinsl-Ober et al. | |
| 6,702,988 B1 * | 3/2004 | Sagona et al. | 422/404 |
| 8,067,243 B2 * | 11/2011 | Erfurth et al. | 436/161 |
| 2002/0025064 A1 | 2/2002 | Itoh | |
| 2006/0101129 A1 * | 5/2006 | Rubertelli et al. | 709/217 |
| 2011/0000763 A1 | 1/2011 | Kimura et al. | |

FOREIGN PATENT DOCUMENTS

| | | |
|---|---|---|
| JP | 63-500546 A | 2/1988 |
| JP | S63-500546 A | 2/1988 |
| JP | 05-196626 A | 8/1993 |
| JP | H5-196626 A | 8/1993 |
| JP | 2000-266757 A | 9/2000 |
| JP | 2002-022748 A | 1/2002 |
| JP | 2003-111733 A | 4/2003 |
| WO | WO 87/00659 A1 | 1/1987 |
| WO | 2009/107817 A1 | 9/2009 |

* cited by examiner

*Primary Examiner* — Christle Marshall
(74) *Attorney, Agent, or Firm* — Fox Rothschild LLP

(57) ABSTRACT

An analytical device is provided that can easily determine whether analysis results are affected by drug administration for the test subject when a sample such as urine or blood is analyzed. The analytical device includes reading means capable of reading test subject identification information recorded on an information recording portion of a sample container, and data output means capable of outputting data on analysis results of a sample contained in the sample container, the analytical device further having: information acquiring means capable of acquiring, from a source external to the analytical device, drug administration information on the test subject corresponding to the test subject identification information read by the reading means, wherein when the data on analysis results of a sample are outputted by the data output means, data on the drug administration information on the test subject corresponding thereto are also outputted.

11 Claims, 13 Drawing Sheets

FIG.5

| MEASUREMENT ITEM | DRUG | EFFECT |
|---|---|---|
| GLUCOSE (GLU) | TIMIPERONE<br>ASCORBIC ACID<br>AMPICILLIN<br>⋮ | FALSE POSITIVE<br>FALSE NEGATIVE<br>FALSE NEGATIVE |
| PROTEINS (PRO) | MAGNESIUM CITRATE<br>CIBENZOLINE SUCCINATE<br>⋮ | FALSE POSITIVE<br>FALSE POSITIVE |
| UROBILINOGEN (URO) | OPHTHALM K PILLS<br>SULFISOXAZOLE<br>p-AMINOBENZOIC ACID<br>⋮ | FALSE POSITIVE<br>FALSE POSITIVE<br>FALSE NEGATIVE |
| BILIRUBIN (BIL) | IOBENZAMIC ACID<br>ETODOLAC<br>EPALRESTAT<br>ASCORBIC ACID<br>⋮ | FALSE POSITIVE<br>FALSE POSITIVE<br>FALSE POSITIVE<br>FALSE NEGATIVE |
| CREATININE | CIMETIDINE<br>⋮ | FALSE POSITIVE |
| pH | MAGNESIUM CITRATE<br>⋮ | FALSE POSITIVE |
| OCCULT BLOOD (BLD) | ASCORBIC ACID<br>OPHTHALM K PILLS<br>CAPTOPRIL<br>⋮ | FALSE NEGATIVE<br>FALSE NEGATIVE<br>FALSE NEGATIVE |
| KETONE BODY (KET) | ALACEPRIL<br>EPALRESTAT<br>⋮ | FALSE POSITIVE<br>FALSE POSITIVE |
| NITRITE (NIT) | ASCORBIC ACID<br>⋮ | FALSE NEGATIVE |
| LEUCOCYTES (LEU) | TETRACYCLINE<br>CEPHALEXIN<br>⋮ | FALSE NEGATIVE<br>FALSE NEGATIVE |

D1

DATA OUTPUT METHOD IN ANALYSIS OF SAMPLE, ANALYTICAL DEVICE, AND ANALYTICAL SYSTEM

BACKGROUND OF THE INVENTION

1. Field of the Invention

The present invention relates to a technique for analyzing a sample such as urine and blood and outputting data such as the analysis results.

2. Description of the Related Art

An analytical device for analyzing a sample such as urine or blood is known in which, in addition to performing analysis of the sample, information (test subject identification information) for identifying the test subject, who is the person providing the sample, is read from an information recording portion such as a barcode attached to a sample container (see, for example, Japanese Patent Application Publication No. H5-196626). When analysis results of the sample are printed by a printer in such an analytical device, the test subject identification information can be printed together with the analysis results. As a result, it is possible to determine adequately the person corresponding to the analysis results.

However, there is still room for improvement in the above-described conventional technique.

Thus, when analysis of a sample such as urine or blood is conducted, where a test subject receives drug administration, the values of analytical results sometimes differ from the true values due to the effect of the drug. However, in the above-described conventional technique, when a sample is analyzed by using the analytical device, only the analysis results and data on test subject identification information are outputted, whereas the drug administration information on the test subject is not outputted. Accordingly, it is difficult to determine in an easy manner and accurately whether or not the analysis results are affected by drug administration. Further, in the conventional process, when an examiner conducting a test by using the analytical device has come up with questions concerning the analysis results of a sample, the examiner should look into the status of drug administration to the test subject by referring to the medical records of the test subject. This is also a troublesome operation.

A system described in Japanese Patent Application Publication No. S63-500546 is also known. In this system, the results of health diagnostic and other types of information relating to a plurality of test subjects are all together managed by using a computer network. However, in this system when data on analysis results of a sample are outputted from the analytical device, data on drug administration information on the test subject cannot be outputted and it is difficult to determine in an easy manner and accurately whether or not the analysis results are affected by drug administration.

SUMMARY OF THE INVENTION

The present invention was created with the foregoing in view and it is an object of the present invention to provide a data output method in analysis of a sample, an analytical device, an analytical system, a program for implementing the method, and a recording medium for the program that make it possible to determine easily whether or not the results of analysis of a sample such as urine or blood are affected by drug administered to the test subject.

In accordance with the present invention, the following technical means is used to attain the abovementioned object.

A data output method in analysis of a sample provided according to the first aspect of the present invention includes: a step of reading test subject identification information recorded on an information recording portion of a sample container by reading means provided at an analytical device; a data output step of outputting data on analysis results of a sample contained in the sample container by using a data output means provided at the analytical device, the data output method further including: a step of acquiring, from a source external to the analytical device, drug administration information on the test subject corresponding to the test subject identification information read out by the reading means, wherein when the data on analysis results of a sample are outputted in the data output step, data on the drug administration information on the test subject are also outputted.

The analytical device provided according to the second aspect of the present invention includes: reading means capable of reading test subject identification information recorded on an information recording portion of a sample container, and data output means capable of outputting data on analysis results of a sample contained in the sample container, the analytical device further including: information acquiring means capable of acquiring, from a source external to the analytical device, drug administration information on the test subject corresponding to the test subject identification information read by the reading means, wherein when the data on analysis results of a sample are outputted by the data output means, data on the drug administration information on the test subject corresponding thereto are also outputted.

In the preferred embodiment of the present invention, the information acquiring means includes a communication unit capable of performing data communication with an external information processing device storing the drug administration information, and can acquire the drug administration information from the information processing device.

In the preferred embodiment of the present invention, when in the information recording portion of the sample container the drug administration information on the test subject has been recorded together with the test subject identification information, the reading means can also read the drug administration information, and the information acquiring means is configured to include the reading means.

In the preferred embodiment of the present invention, there is further included determination means for determining whether contents of the drug administration information are contents affecting the analysis results of the sample, wherein in the case in which the determination means determines that the contents of the drug administration information are contents affecting the analysis results of the sample and when the data on the analysis results are outputted, the data on the drug administration information are outputted together therewith, and in the case in which the determination means determines that the contents of the drug administration information are not contents affecting the analysis results of the sample and when the data on the analysis results are outputted, the data on the drug administration information are not outputted together therewith, or data indicating that drug administration produces no effect on the analysis results are outputted together with the drug administration information.

In the preferred embodiment of the present invention, the sample is analyzed in terms of a plurality of items, and in the case in which the determination means determines that the contents of the drug administration information are contents affecting the analysis results of the sample, additional data indicating which item of the plurality of items is affected are outputted together with the drug administration information.

In the preferred embodiment of the present invention, the determination means stores data indicating a correspondence relationship between a specific component in the sample and a drug producing effect on analysis results of this specific component, and the determination of whether or not the contents of the drug administration information are contents affecting the analysis results of the sample is performed on the basis of the data indicating the correspondence relationship.

The analytical system according to the third aspect of the present invention includes: an analytical device and an information processing device that can perform data communication with the analytical device, wherein the analytical device includes reading means capable of reading test subject identification information recorded on an information recording portion of a sample container, and data output means capable of outputting data on analysis results of a sample contained in the sample container, wherein the information processing device stores drug administration information relating to the test subject, the analytical device can acquire, from the information processing device, drug administration information on the test subject corresponding to the test subject identification information read by the reading means, and when the data on the analysis results are outputted by the data output means, data on the drug administration information on the test subject corresponding thereto are also outputted.

In the preferred embodiment of the present invention, the information processing device can determine whether contents of the drug administration information are contents affecting the analysis results of the sample and is configured to transmit data on the determination results to the analytical device.

The program provided according to the fourth aspect of the present invention is used for operating an analytical device including: reading means capable of reading test subject identification information recorded on an information recording portion of a sample container, data output means capable of outputting data on analysis results of a sample contained in the sample container, and control means capable of transmitting data on the data output means, the program including data for executing by control of the control means: a step of acquiring, from a source external to the analytical device, drug administration information on the test subject corresponding to the test subject identification information read out by the reading means, and a step of outputting data on the drug administration information on the test subject corresponding to analysis data together therewith when data on the analysis results are outputted by the data output means.

The recording medium provided according to the fifth aspect of the present invention records the program provided according to the fourth aspect of the present invention.

Other features and merits of the present invention will become more apparent from the description of embodiments of the invention presented below with reference to the appended drawings.

BRIEF DESCRIPTION OF THE DRAWINGS

FIG. 5 is an explanatory drawing illustrating a specific example of data showing the relationship between a sample component and a drug affecting the analysis results of the component;

DESCRIPTION OF THE PREFERRED EMBODIMENTS

The preferred embodiments of the present invention will be described below in greater detail with reference to the appended drawings.

Figure 1:
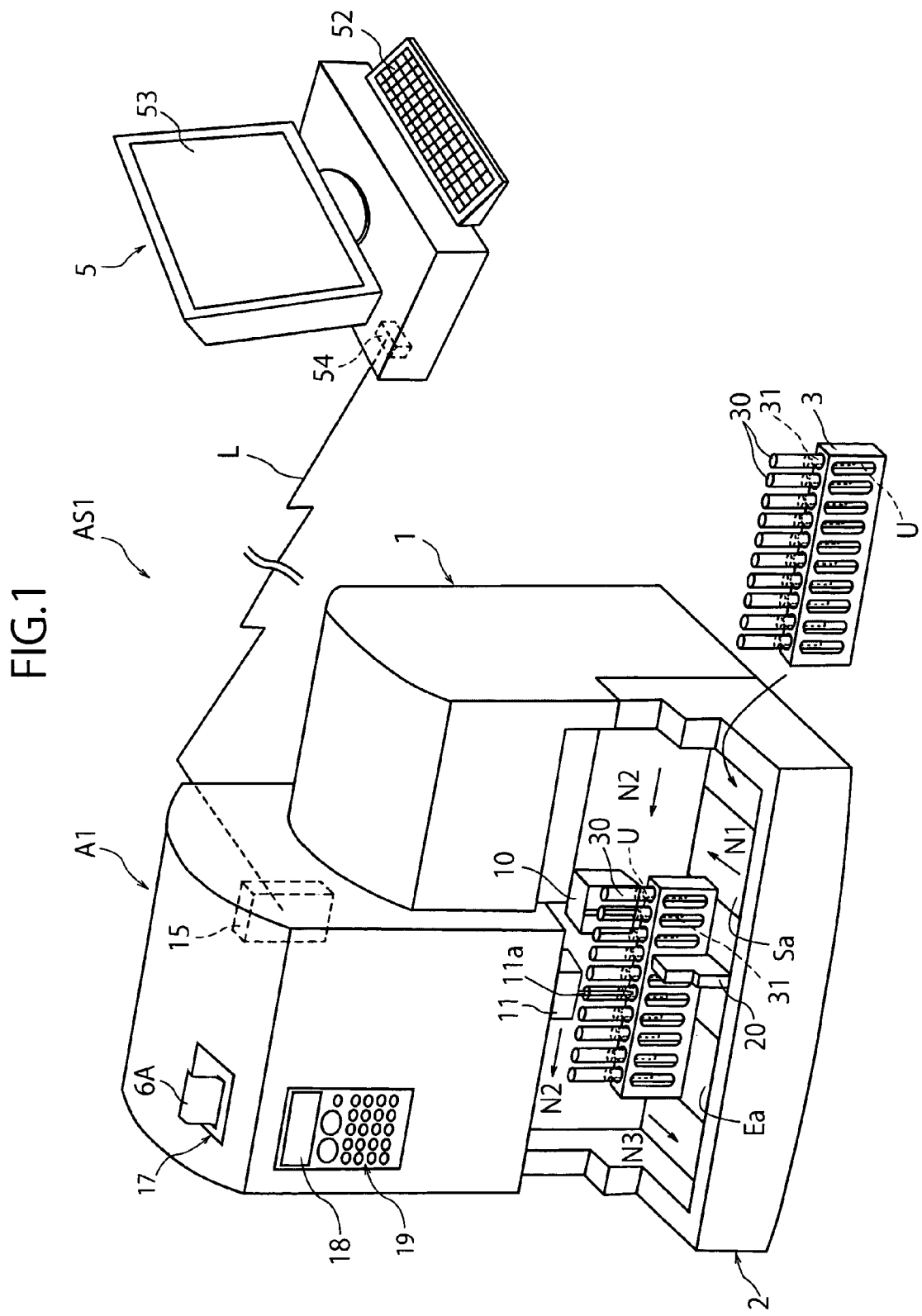
FIG. 1 is a schematic perspective view illustrating an example of the analytical system including the analytical device in accordance with the present invention.

FIGS. 1 to 4 illustrate an example of an analytical device using the present invention and an analytical system using the analytical device. As shown in FIG. 1, an analytical system AS1 of the present embodiment includes an analytical device A1 and an information processing device 5. The analytical system AS1 is installed, for example, in a hospital, and the analytical device A1 and the information processing device 5 are connected by a communication line L. However, since any communication means can be used, provided that the analytical device A1 and the information processing device 5 could exchange data, the two units can be communicatively connected, for example, by using an internal information communication network (LAN) created in the hospital, or a circuit such as internet.

The analytical device A1 serves to perform analysis of urine U contained in a sample container 30 and has an analytical device body unit 1 and a conveyance device 2. The urine U corresponds to an example of sample referred to in the description of the present invention.

The conveyance device 2 serves to convey a rack 3 in which sample containers 30 are held vertically along a predetermined path. A device having a configuration similar to the conventional well-known conveyance device (for example, the conveyance device described in Japanese Patent Application Publication No. 2009-229233) can be used as the conveyance device 2, and details concerning the specific configuration of the conveyance device are herein omitted. Where the rack 3 is loaded in a predetermined start area Sa in the conveyance device 2, the rack 3 is then successively conveyed in the direction shown by arrows N1 to N3 and finally arrives at a predetermined end area Ea. Reading of the below-described barcode and sampling of urine U from the sample container 30 are performed in the process of conveying the rack 3 in the direction of the arrow N2.

Figure 3:
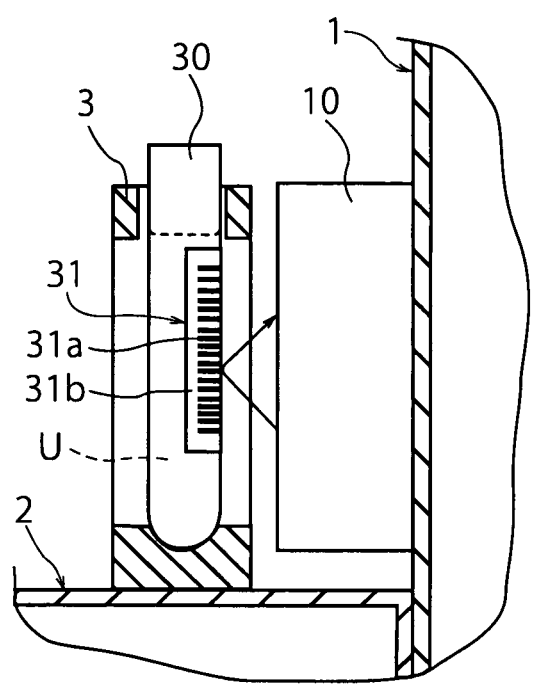
FIG. 3 is a principal cross-sectional view illustrating an example of the reading unit of the analytical device and the information recording portion of the sample container shown in FIG. 1.
Figure 4:
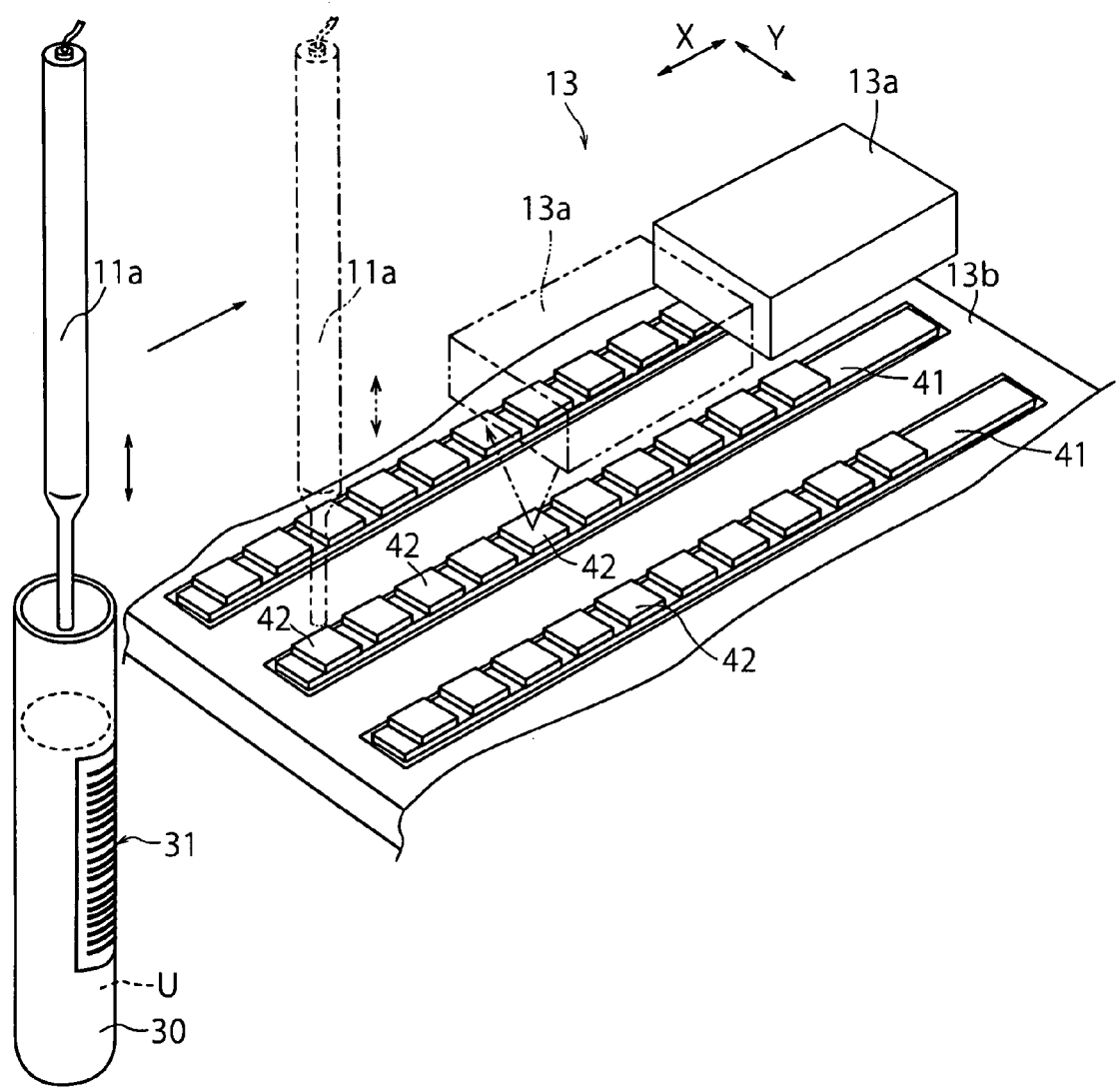
FIG. 4 is a principal perspective view illustrating the analytical unit of the analytical device shown in FIG. 1.

The analytical device body unit 1 includes a reading unit 10, a suction nozzle 11a, and the below-described devices. As shown in FIG. 3, the sample container 30 is provided, for example, with an information recording section 31 constituted by using a label 31b where a barcode 31a has been printed. Test subject identification information for identifying the test subject who provided the urine U is recorded at the information recording section 31. The reading unit 10 is for example a barcode reader. Where the sample container 30 is conveyed to the front surface of the reading unit, the test subject identification information is read from the information recording section 31 of the sample container 30. The suction nozzle 11a serves for sucking and sampling the predetermined amount of urine U from the sample container 30 that passed by the front surface of the reading unit 10. The urine U sampled by the suction nozzle 11a is supplied for analysis to the below-described analytical unit 13.

Figure 2:
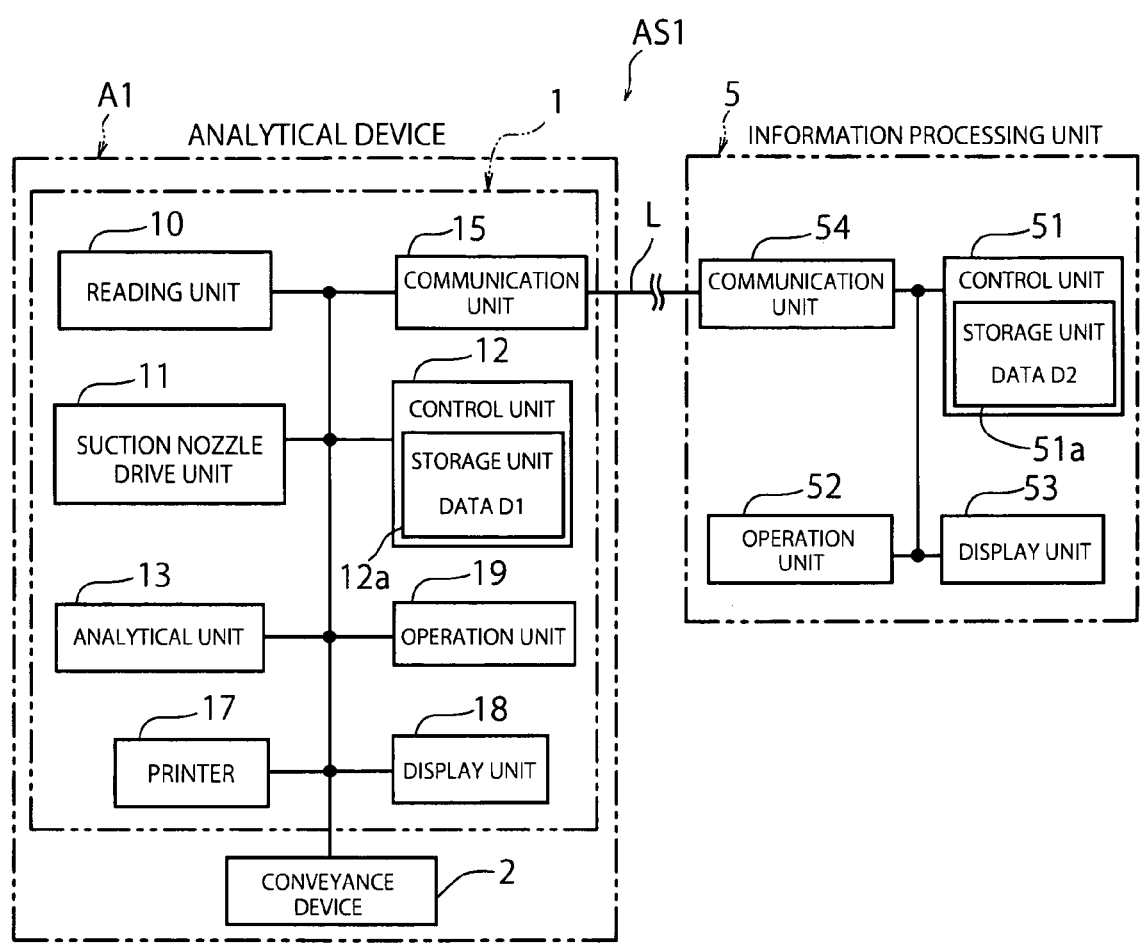
FIG. 2 is a block diagram of the analytical system shown in FIG. 1.

As shown in FIG. 2, the analytical device A1 includes a suction nozzle drive unit 11, a control unit 12, an analytical unit 13, a communication unit 15, a printer 17, a display unit 18, and an operation unit 19 in addition to the aforementioned reading unit 10 and conveyance unit 2.

The suction nozzle drive unit 11 is provided with a mechanism (not shown in the figure) for sampling the urine U by using the suction nozzle 11a and dispensing the sampled urine U to a predetermined position of the analytical unit 13. A unit configured similarly to the analytical unit used in the conventional well-known analytical device (for example, the analytical device described in Patent Publication No. 2561509 or WO 2006/112470) can be used as the analytical unit 13. The analytical unit 13 will be described below in a simple manner with reference to FIG. 14. The analytical unit 13 is provided with a plurality of test pieces 41 arranged on a table 13b and an optical measurement device 13a. Each test piece 41 is provided with a plurality of reagent pads 42, and the urine U sampled by the suction nozzle 11a is dispensed onto these reagent pads 42. The plurality of reagent pads 42 are configured to react with the predetermined component contained in the urine and develop a color to a degree corresponding to the concentration of the component. The optical measurement device 13a can move in the X and Y directions and can measure the color development degree (light reflectance and the like) of each reagent pad 42 onto which the urine U has landed. The concentration of the predetermined component in the urine is calculated on the basis of the measurement data on the optical measurement device 13a.

Referring to FIG. 2, the printer 17 serves to output by printing the data on the analysis results of urine U and test subject identification information onto predetermined paper and corresponds to an example of a data output means in accordance with the present invention. As described hereinbelow, the printer also prints, when requested, on the paper the data on the drug administration information on the test subject. The display unit 18 is provided with an image display screen such as a liquid crystal display panel and performs image display, for example, for guiding the operation of the operation unit 19. However, the display unit 18 may also display the analysis result of urine U. In this case, the display unit 18 corresponds to a specific example of the data output means in accordance with the present invention.

The control unit 12 is configured by using, for sample, a microcomputer and includes a storage unit 12a. The control unit 12 corresponds to an example of the control means or determination means in accordance with the present invention. The storage unit 12a stores a program or various data for executing the operation control of units of the analytical device A1 and data processing of various kinds by the control unit 12.

Data stored in the storage unit 12a include data D1 indicating the relationship between the predetermined component contained in the urine and the drug producing effect on the analysis result of this component. The data D1 have the contents, for example, such as shown in FIG. 5. When Timiperone is administered to the test subject, the analysis results of the glucose (GLU) in urine can easily become falsely positive, and when ascorbic acid or ampicillin is administered, the results can easily become falsely negative. Reflect by these features, in the data D1, Timiperone, ascorbic acid, and ampicillin are presented as examples of drugs affecting the analysis results of glucose in urine. The data D1 similarly include the correspondence relationship between components contained in urine, such as protein (PRO), urobilinogen (URO), bilirubin (BIL), creatinine (CRE), pH, occult blood (BLD), ketone body (KET), nitrite (NIT), and leucocytes (LEU), and drugs that are highly probable to produce a negative effect on the analysis results of the components. After the analysis of urine U has been completed, these data D1 are referred to and used to determine where the analysis results of the urine U have been affected by the administration of drugs to the test subject.

The information processing device 5 is construed by using, for example a personal computer. As shown in FIG. 2, the information processing device includes a control unit 51 having a storage unit 51a, a display unit 53, an operation unit 52, and a communication unit 54. The information processing device 5 serves, to manage or verify, for example, test subject identification information with respect to a large number of test subjects (including patients) visiting the hospital where the analytical system AS1 is disposed, history of hospital visits, prescription history, history of health diagnostic result, and various other types of information. The storage unit 51a stores data D2 of drug administration information. These data D2 correspond to the aforementioned prescription history and include, for example, information indicating the name and amount of the drug prescribed to the test subject, prescription date, and the diagnosed illness against which the drug has been prescribed.

The communication unit 15 of the analytical device A1 is used to acquire drug administration information from the information processing device 5 and corresponds to an example of the information acquiring means in accordance with the present invention. It goes without saying that the communication unit 15 can be used for other communication applications. When the analysis of urine U is completed and the analysis results are printed with the printer 17, the control unit 12 causes the printer to print also the aforementioned drug administration information, when this is required. This process will be described below in greater detail.

An example of data output method used when the analysis of urine U is implemented by using the analytical device A1 and an example of operation processing procedure of the control unit 12 of the analytical device A1 will be explained below with reference to the flowchart shown in FIG. 6.

Where the sample container 30 arrives at a predetermined position a process in which the conveyance device 2 is driven and the rack 3 is conveyed along the abovementioned predetermined path, the test subject identification information is read from the information recording portion 31 of the sample container 30 by the reading unit 10 (S1). Accordingly, the control unit 12 accesses the information processing device 5 and verifies whether or not the data D2 of the drug administration information corresponding to the test subject identification information have been stored in the storage unit 51a (S2).

Where the verification result indicates that the data D2 of the drug administration information corresponding to the test subject identification information have been stored in the storage unit 51a, the control unit 12 acquires the data D2 and temporarily stores the acquired data in the storage unit 12a (S3: YES, S4). Where the sample container 30 then arrives at the predetermined sample sampling position, the control unit 12 samples the urine U from the sample container 30 by using the suction nozzle 11a and implements the analysis of urine U in the analytical unit 13 (S5).

The control unit 12 also determines whether or not the contents of the drug administration information (data D2) acquired from the information processing device 5 are the contents affecting the analysis results of the urine U (S6). When such determination is performed, the control unit refers to the data D1 explained with reference to FIG. 5. Therefore, for example, when birulibin (BIL) and ketone body (KET) are considered as the analysis items of urine U and Epalrestat has been administered to the test subject, the control unit 12 determines that the contents of the drug administration information affects the analysis results of urine U. It is preferred that this determination be performed by also taking into account the period in which the drug has been administered to the test subject, rather than only on the relationship between the analysis item and the administered drug. For example, where information relating to the prescription date and amount of drug (daily dose) is present in the drug administration information, the final date of drug administration can be specified. Therefore, when the final date of drug administration precedes the present time by a predetermined number of days or a longer interval, the drug can be determined to produce no effect.

Figure 7:
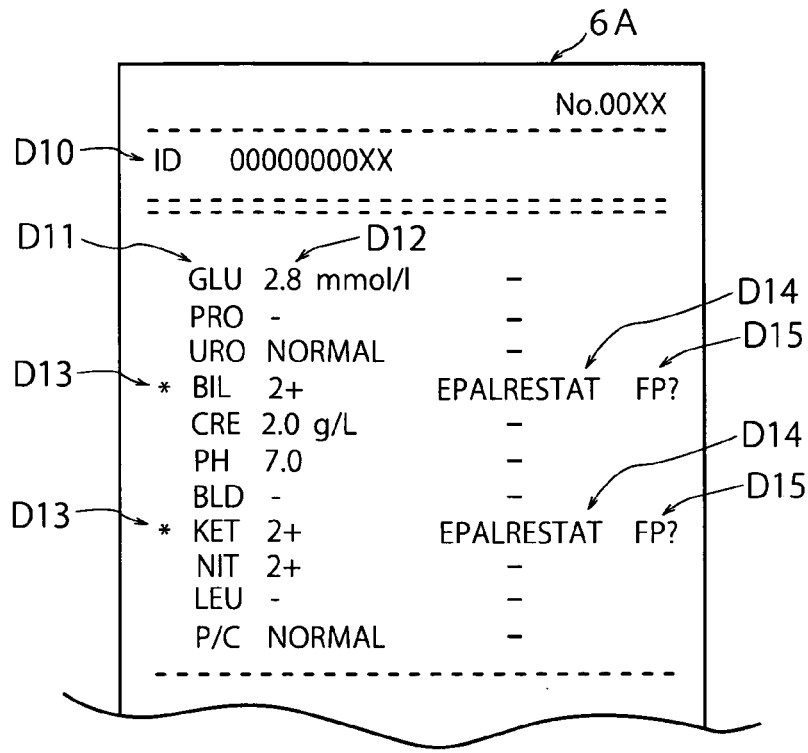
FIG. 7 shows an example of the report outputted by the analytical device shown in FIG. 1.

When the control unit 12 determines that the contents of the drug administration information affect the analysis results of urine U (S7: YES), where the analysis results of urine U are printed on the predetermined paper by the printer 17, the drug administration information is also printed together therewith. As a result, a report 6A, for example such as shown in FIG. 7, is created. In the report 6A, data D10 for test subject identification, data D11 of analysis items, and data D12 of analysis results are outputted by printing. In addition, data 13 for specifying analysis items affected by drug administration, data 14 indicating the name of the administered drug, and data D15 indicating the contents of the effect produced by the drug on the analysis results are also outputted by printing. In the figure, the data D13 are displayed by using a symbol "*", but other symbols, letters, or drawings can be also used. For example, when Epalrestat is administered to the test subject, the analytical values of birulibin (BIL) and ketone body (KET) are affected. Therefore, data D13 to D15 are outputted by printing to the locations corresponding to the birulibin (BIL) and ketone body (KET) items in the data D11 on the analysis items. Data D15 are displayed as "FP?" in the figure, this designation indicating the uncertainty of false positivity. In addition to the above-described information, the report 6A may also additionally include data relating to the drug prescription date, administration dose, or final date of administration.

Where the above-described report 6A is created, the person using the analytical device A1 to conduct the test can easily and rapidly determine that the drug administered to the test subject is highly probable to affect the analysis results of urine U. The resultant merit is that it is possible to eliminate or reduce the probability of erroneously recognizing as correct those values of the analysis results of urine U that have been affected by drug administration and are inherently incorrect. Further, the person conducting the test is not required, for example, to operate the information processing device 5 and conduct troublesome investigation of the prescription history of the test subject and the load on the person conducting the test can be reduced. In particular, the report 6A makes it possible to distinguish easily the analysis items that are highly probable to be affected by drug administration from those which are not. Therefore, it is not necessary to investigate whether the analysis results have been affected by drug administration with respect to each of the analysis items and the load on the person conducting the test can be further reduced.

Figure 8:
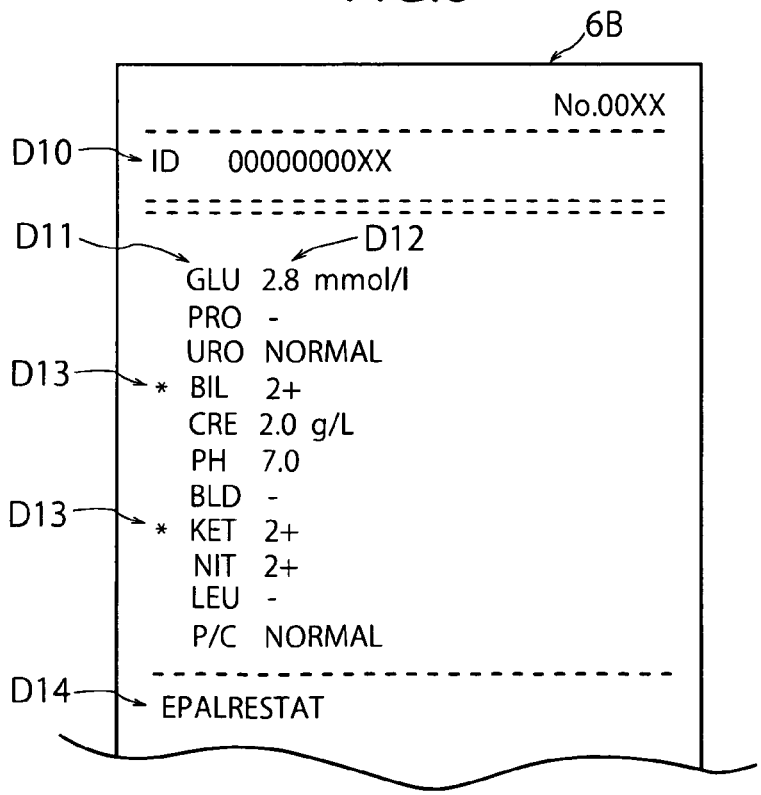
FIG. 8 shows another example of a report outputted by the analytical device shown in FIG. 1.

When the analysis results and drug administration information are printed together, reports that are different in form from the above-described report 6A can be created. Thus, in the report 6B shown in FIG. 8, data D14 indicating the name of the drug that has been administered are not disposed correspondingly to the data D11 of the analysis items. However, the analysis item affected by drug administration can be accurately recognized by the presence of data D13. In accordance with the present invention, data D13 and D15 can be omitted and only data D14 indicating the name of the administered drug can be outputted by printing as the drug administration information (such a configuration is not shown in the figures). The person conducting the test can comparatively easily recognize the analysis items that are highly probable to be affected by the drug on the basis on the name of the administered drug indicated by data D14, and the load on the person conducting the test can be reduced by comparison with the case in which data D14 are not outputted by printing.

Figure 9:
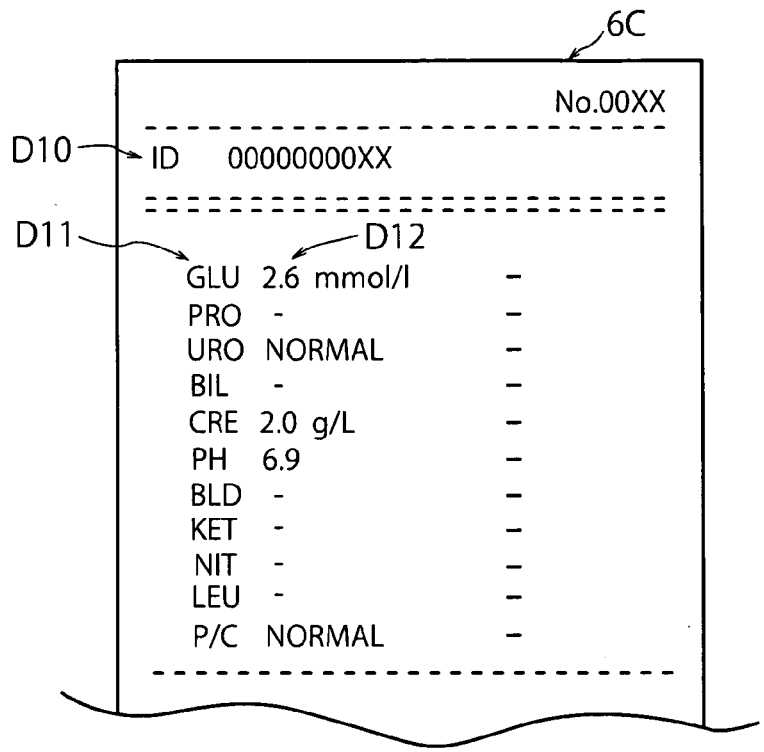
FIG. 9 shows another example of a report outputted by the analytical device shown in FIG. 1.

By contrast with the abovementioned case, when data D2 of the drug administration information corresponding to the test subject identification information is not stored in the information processing device (S3: NO), the control unit 12 does not create the reports of the above-described form. Further, even if data D2 of the drug administration information are stored in the information processing device 5, where the contents of the drug administration information is determined not to be the contents affecting the analysis results of urine U (S7: NO), the control unit 12 also does not create the reports of the above-described form. In such a case, at the point of time in which the sample container 30 arrives at the predetermined sample sampling position, the control unit 12 performs control to sample and analyze the urine U and also to print the analysis results on the predetermined paper with the printer 17 (S9, S10). As a result, for example, a report 6C such as shown in FIG. 9 is created. In the report 6C, data D10 for test subject identification, data D11 of analysis items, and data D12 of the analysis results are printed, but the drug administration information is not printed. When such report 6C is created, the person conducting the test by using the analytical device A1 can promptly recognize that the analysis results of urine U are the correct results that are not affected by drug administration.

Figure 10:
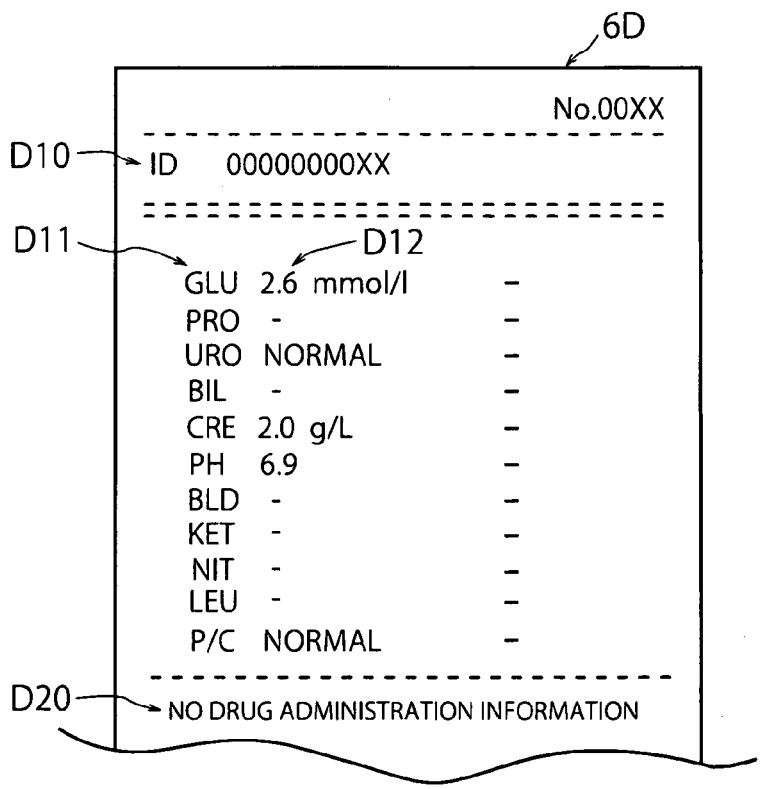
FIG. 10 shows another example of a report outputted by the analytical device shown in FIG. 1.
Figure 11:
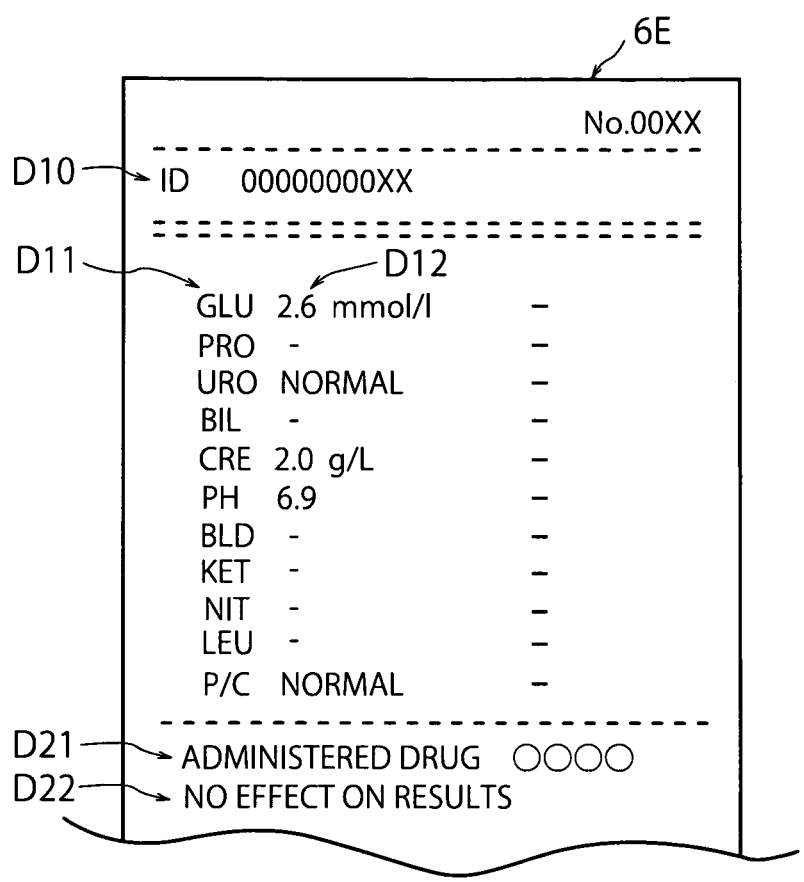
FIG. 11 shows another example of a report outputted by the analytical device shown in FIG. 1.

When the analysis results of urine U are not affected by drug administration, for example, reports 6D, 6E such as shown in FIG. 10 and FIG. 11 can be created as report of the form different from that of the above-described report 6C. More specifically, when data D2 of drug administration information corresponding to the test subject identification information are not stored in the information processing device 5, data D20 clearly indicating that the drug administration information is not present can be outputted by printing, as in the report 6D. Where data D2 of the drug administration information have been printed in the information processing device 5 and the contents of the drug administration information is determined not to be the contents affecting the analysis results, data D21 indicating the name of the administered drug and also data D22 clearly indicating that this drug produces no effect on the analysis results can be outputted by printing as in the report 6E. In this case, data such as a drug prescription date or a final date of drug administration may be additionally printed.

Another example of operation processing procedure of the control unit 12 will be described below with reference to the flowchart shown in FIG. 12.

Figure 13:
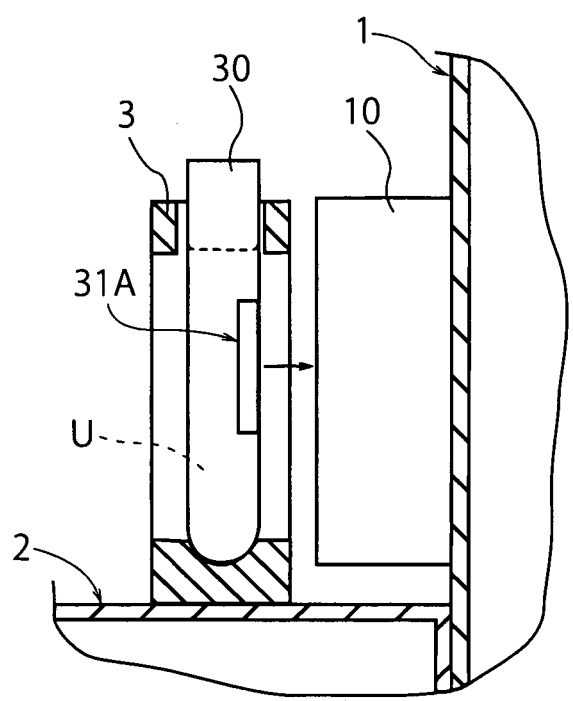
FIG. 13 is a principal cross-sectional view illustrating another example of the reading unit of the analytical device and the information recording portion of the sample container shown in FIG. 1.

The below-described configuration is a precondition for implementing the operation processing of the present embodiment. Thus, as shown in FIG. 13, test subject identification information and drug administration information corresponding to the test subject identification information are recorded on the information recording portion 31A provided at the sample container 30. It is also possible that the drug administration information corresponding to the test subject identification information be not present. Since the amount of information recorded on the information recording portion 31A becomes comparatively large, it is preferred that the information recording portion be constituted by using an IC tag. In this case, the reading unit 10 is constituted by using an IC tag reader instead of, or in addition to the barcode reader. It goes without saying that a configuration using a two-dimensional code that makes it possible to increase the amount of recorded information and a configuration using a plurality of barcodes be used instead of the IC tag of the information recording portion 31A.

Figure 6:
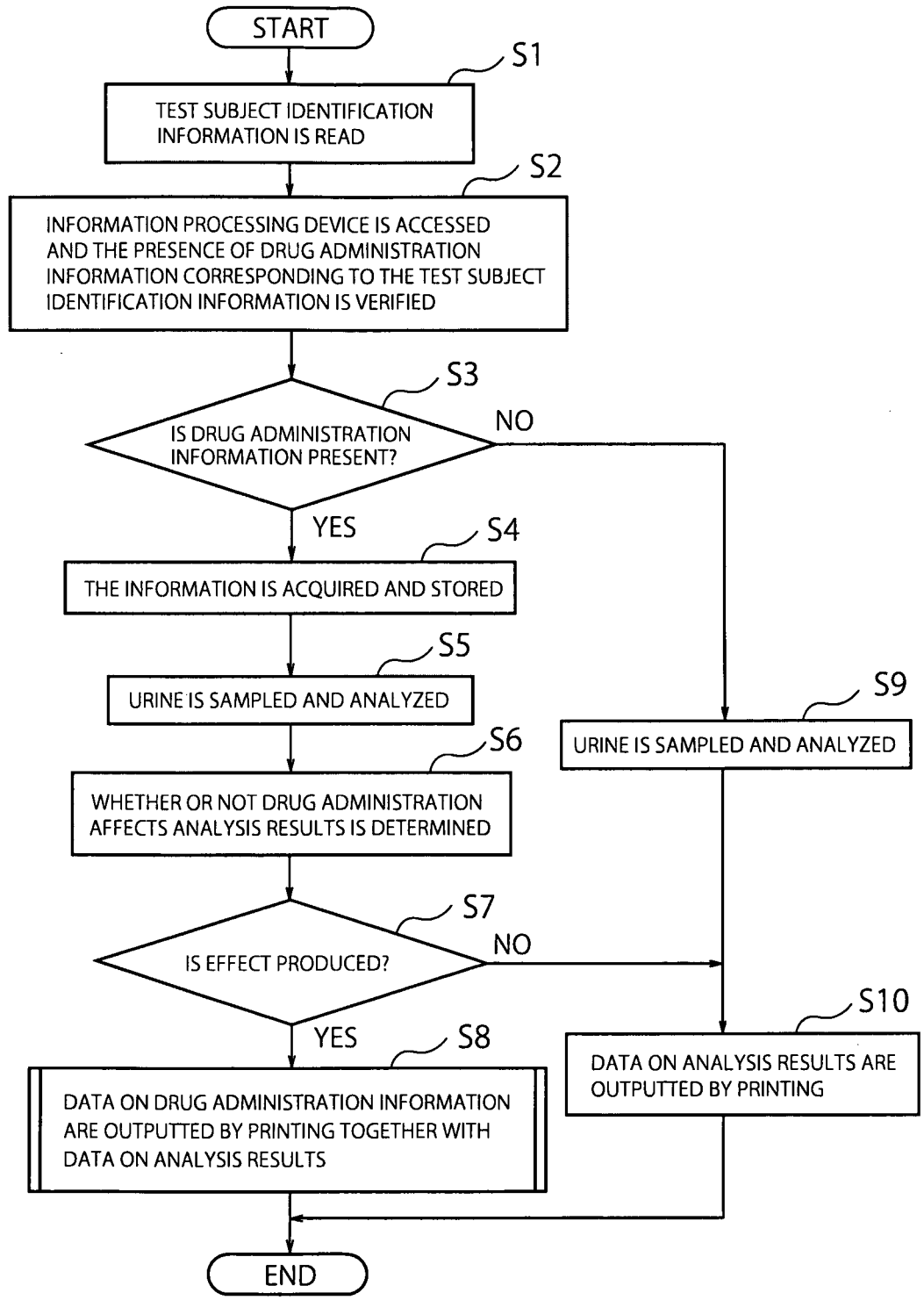
FIG. 6 is a flowchart illustrating an example of the operation processing procedure of the control unit of the analytical device shown in FIG. 1.
Figure 12:
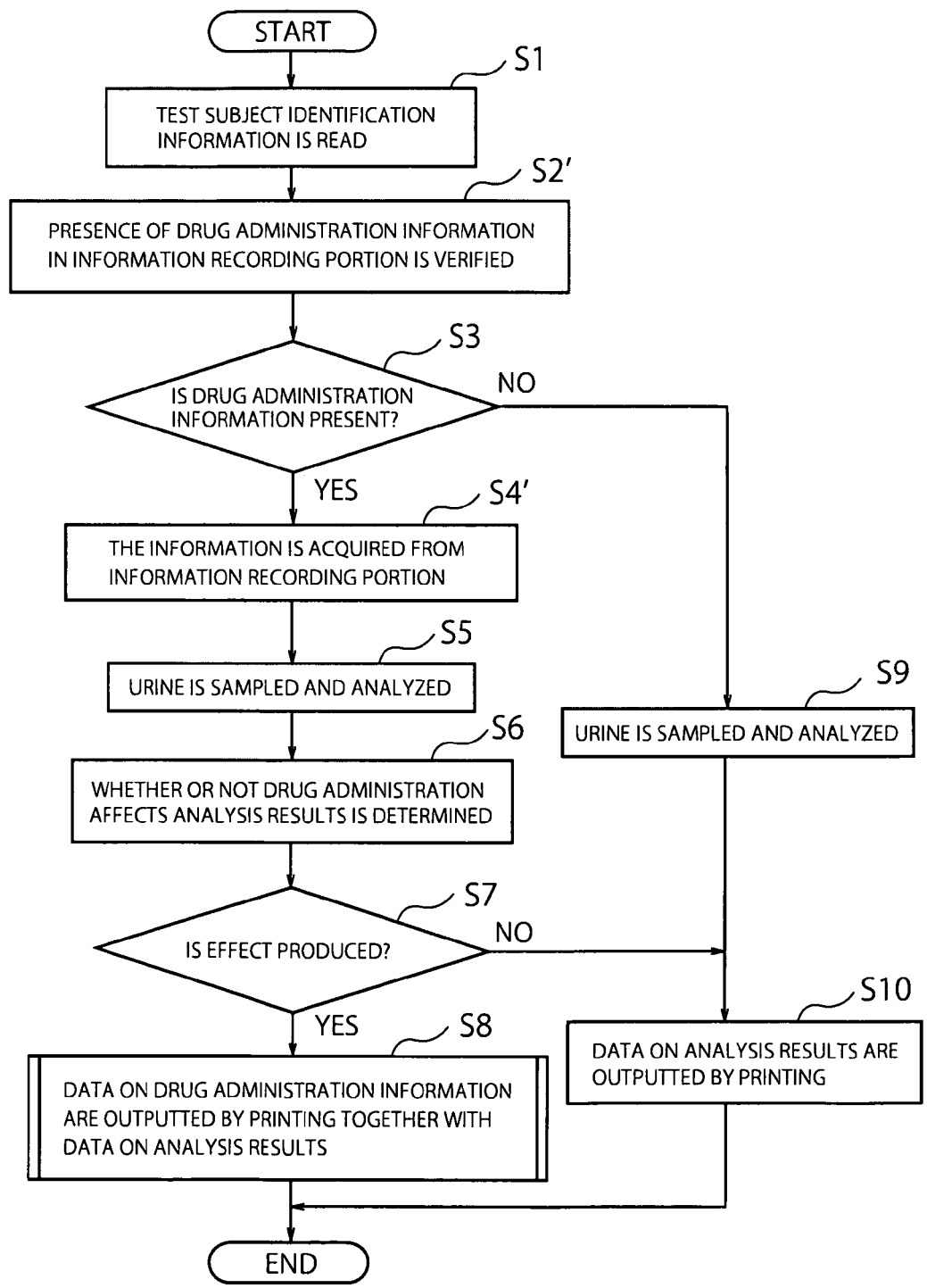
FIG. 12 is a flowchart illustrating another example of an operation processing procedure of the control unit of the analytical device shown in FIG. 1.

In the flowchart shown in FIG. 12, although steps S2', S4' are different from the steps S2, S4 of the flowchart shown in FIG. 6, other steps are similar to those shown in FIG. 6. In the present embodiment, when the test subject identification information is read from the information recording portion 31A of the sample container 30 (S1), the control unit 12 verifies whether or not the drug administration information has been recorded on the information recording portion 31 (S2'). When the drug administration information has been recorded on the information recording portion 31A, the control unit 12 performs control such that the drug administration information is read from the information recording portion 31A by using the reading unit 10 and the data on the drug administration information are stored (S3: YES, S4'). Therefore, in the present embodiment, the reading unit 10 corresponds to a specific example of the information acquiring means in accordance with the present invention. In step S4' and subsequent steps, the processing is performed that is similar to that explained with reference to FIG. 6.

In the present embodiment, the drug administration information is not required to be acquired from the information processing device 5. Therefore, reports similar to the reports 6A to 6E shown in FIGS. 7 to 11 can be adequately created, while using the analytical device A1 independently, that is, without communicative connection to the information processing device 5.

Figure 14:
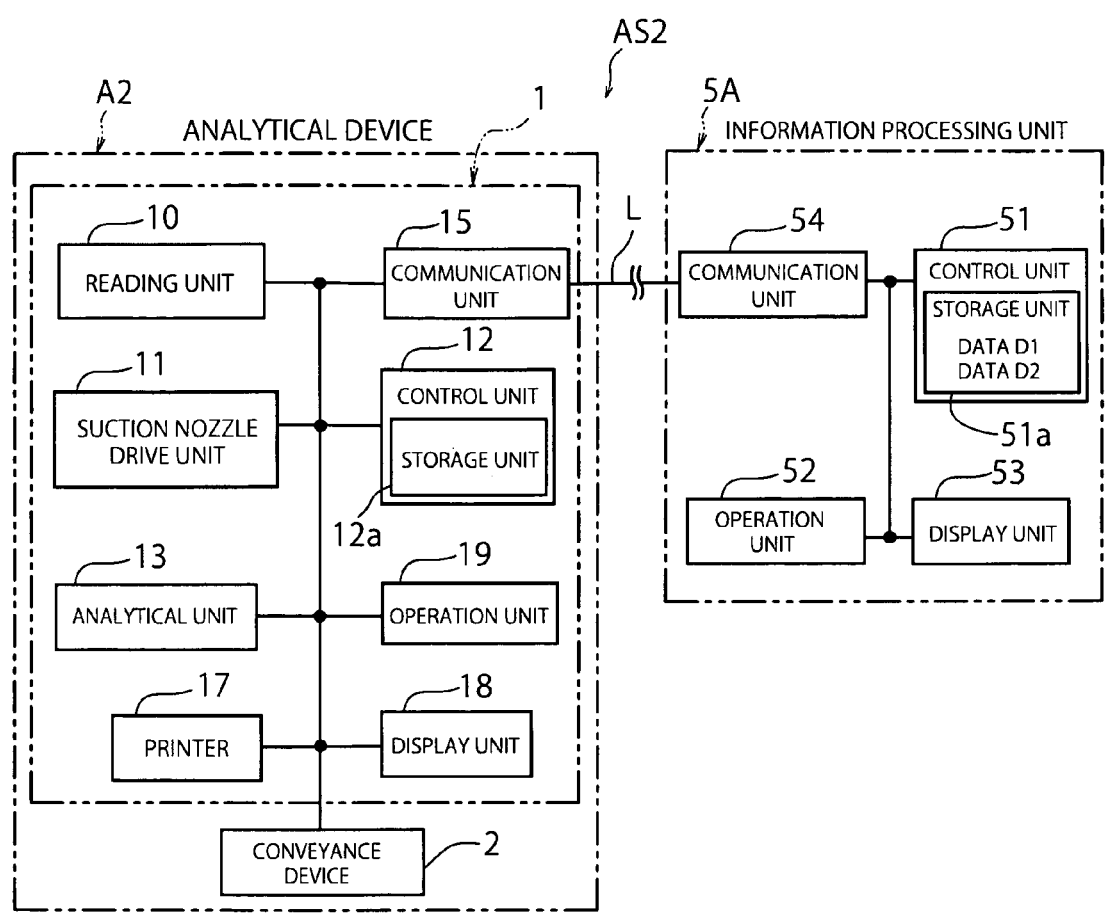
FIG. 14 is a block diagram illustrating another example of the analytical system including the analytical device in accordance with the present invention.

FIG. 14 illustrates another embodiment of the analytical system in accordance with the present invention. In the figure, elements identical or similar to those of the above-described embodiments are assigned with identical reference symbols.

Figure 15:
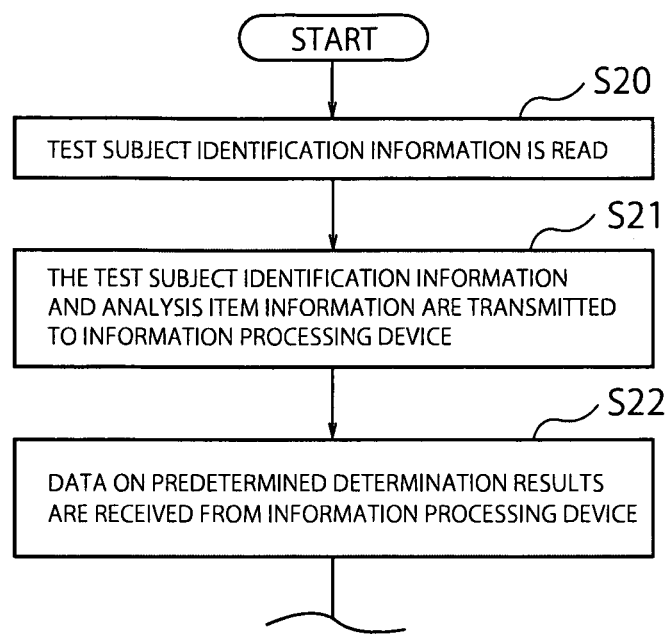
FIG. 15 is a flowchart illustrating an example of part of the operation processing procedure of the control unit of the analytical device shown in FIG. 14.

In the analytical system AS2 shown in FIG. 14, data D1 indicating the relationship between the components of urine and drugs affecting the analysis results of the components are stored in the control unit 51 of the information processing device 5A and not stored in the control unit 12 of the analytical device A2. The control unit 12 of the analytical device A2 is configured such that where the test subject identification information is read from the information recording portion 31 of the sample container 30 (S20), as shown in the flowchart in FIG. 15, information relating to the analysis item of urine is thereafter transmitted together with the test subject identification information to the information processing device 5A via the communication unit 15 (S21). Where the control unit 51 of the information processing device 5A receives the aforementioned information from the analytical device A2, the control unit determines whether or not the drug administration affects the analysis results of urine on the basis of data D1, D2 stored in the control unit 51. The data on the determination results are received by the control unit 12 of the analytical device A2 (S22).

With the present embodiment, reports similar to the above-described reports 6A to 6E can be created on the basis of data on the determination results obtained by processing in the information processing device 5A. In the present embodiment, it is not necessary to store data D1 in the control unit 12 of the analytical device A2 and also it is not necessary to implement in the control unit 12 the determination as to whether or not the drug administration affects the analysis results of urine U. The advantageous result is that the data processing load of the control unit 12 can be reduced and the analytical device A2 can be reduced in cost.

The present invention is not limited to the above-described embodiments.

The drug administration information in accordance with the present invention may include no other information such as a drug prescription date, provided that the drug administration information include at least information specifying the drug (the name of the drug does not necessarily have to be included in this information) that has been administered to the test subject. The data output means in accordance with the present invention is not limited to the printer or display device. For example, the communication unit 15 shown in FIG. 2 can be also used as the data output means in accordance with the present invention.

The sample analyzed in the analytical device and analytical system in accordance with the present invention is not limited to urine and can be blood or other substance and is not generally limited to a specific type of sample. Further, the specific contents of analysis is also not limited. The present invention can be applied not only to a comparatively large analytical device provided with a conveyance device for a sample container, but also to small analytical devices including no such conveyance device.

What is claimed is:

1. A data output method in analysis of a sample, the method comprising:
   a step of reading test subject identification information recorded on an information recording portion of a sample container by reading means provided at an analytical device;
   a data output step of outputting data on analysis results of a sample contained in the sample container by using a data output means provided at the analytical device, the method further comprising:
   a step of acquiring, from a source external to the analytical device, drug administration information on the test subject corresponding to the test subject identification information read out by the reading means, wherein
   when the data on analysis results of a sample are outputted in the data output step, data on the drug administration information on the test subject are also outputted;

a step of determining whether contents of the drug administration information are contents that affect the analysis results of a sample by a determination means, wherein
in the case in which the determination means determines that the contents of the drug administration information are contents that affect the analysis results of a sample and when the data on the analysis results are outputted the data on the drug administration information and data indicating that drug administration produces effect on the analysis results are outputted together therewith, and
in the case in which the determination means determines that the contents of the drug administration information are not contents that affect the analysis results of a sample and when the data on the analysis results are outputted, the data on the drug administration information are not outputted together therewith, or the drug administration information are outputted together therewith.

2. An analytical device comprising:
reading means capable of reading test subject identification information recorded on an information recording portion of a sample container, and
data output means capable of outputting data on analysis results of a sample contained in the sample container,
the analytical device further comprising:
information acquiring means capable of acquiring, from a source external to the analytical device, drug administration information on the test subject corresponding to the test subject identification information read by the reading means, wherein
when the data on analysis results of a sample are outputted by the data output means, data on the drug administration information on the test subject corresponding thereto are also outputted;
determination means for determining whether contents of the drug administration information are contents that affect the analysis results of a sample, wherein
in the case in which the determination means determines that the contents of the drug administration information are contents that affect the analysis results of a sample and when the data on the analysis results are outputted, the data on the drug administration information and data indicating that drug administration produces effect on the analysis results are outputted together therewith, and
in the case in which the determination means determines that the contents of the drug administration information are not contents that affect the analysis results of a sample and when the data on the analysis results are outputted, the data on the drug administration information are not outputted together therewith, or the drug administration information are outputted together therewith.

3. The analytical device according to claim 2, wherein
the information acquiring means includes a communication unit capable of performing data communication with an external information processing device storing the drug administration information, and can acquire the drug administration information from the information processing device.

4. The analytical device according to claim 3, wherein
when in the information recording portion of the sample container the drug administration information on the test subject has been recorded together with the test subject identification information, the reading means can also read the drug administration information, and
the information acquiring means is configured to include the reading means.

5. The analytical device according to claim 4, wherein
the sample is analyzed in terms of a plurality of items, and in the case in which the determination means determines that the contents of the drug administration information are contents affecting the analysis results of a sample, additional data indicating which item of the plurality of items is affected are outputted together with the drug administration information.

6. The analytical device according to claim 3, wherein
the sample is analyzed in terms of a plurality of items, and in the case in which the determination means determines that the contents of the drug administration information are contents affecting the analysis results of a sample, additional data indicating which item of the plurality of items is affected are outputted together with the drug administration information.

7. The analytical device according to claim 2, wherein
when in the information recording portion of the sample container the drug administration information on the test subject has been recorded together with the test subject identification information, the reading means can also read the drug administration information, and
the information acquiring means is configured to include the reading means.

8. The analytical device according to claim 7, wherein
the sample is analyzed in terms of a plurality of items, and in the case in which the determination means determines that the contents of the drug administration information are contents affecting the analysis results of a sample, additional data indicating which item of the plurality of items is affected are outputted together with the drug administration information.

9. The analytical device according to claims 2, wherein
in the case in which the determination means determines that the contents of the drug administration information are not contents affecting the analysis results of a sample and when the data on the analysis results are outputted with the drug administration information, data indicating that drug administration produces no effect on the analysis results are outputted together therewith.

10. The analytical device according to claim 2, wherein
the sample is analyzed in terms of a plurality of items, and in the case in which the determination means determines that the contents of the drug administration information are contents affecting the analysis results of a sample, additional data indicating which item of the plurality of items is affected are outputted together with the drug administration information.

11. An analytical system having an analytical device and an information processing device that can perform data communication with the analytical device, the analytical device having reading means capable of reading test subject identification information recorded on an information recording portion of a sample container, and data output means capable of outputting data on analysis results of a sample contained in the sample container, wherein
the information processing device stores drug administration information relating to the test subject,
the analytical device can acquire, from the information processing device, drug administration information on the test subject corresponding, to the test subject identification information read by the reading means, and
when the data on the analysis results are outputted by the data output means, data on the drug administration information on the test subject corresponding thereto are also outputted, wherein the information processing device can determine whether contents of the drug administration information are contents that affect the analysis results of a sample and is configured to transmit data on the determination results to the analytical device, in the case in which the information processing device determines that the contents of the drug administration information are contents that affect the analysis results of a sample and when the data on the analysis results are outputted, the data on the drug administration information and data indicating that drug administration produces effect on the analysis results are outputted together therewith, and in the case in which the information processing device determines that the contents of the drug administration information are not contents that affect the analysis results of a sample and when the data on the analysis results are outputted, the data on the drug administration information are not outputted together therewith, or the drug administration information are outputted together therewith.

* * * * *